(12) United States Patent
Kim

(10) Patent No.: US 11,549,931 B2
(45) Date of Patent: Jan. 10, 2023

(54) DEVICE FOR MEASURING MOISTURE CONTENT IN SOIL

(71) Applicant: TELOFARM, INC., Seoul (KR)

(72) Inventor: Woo Joong Kim, Gyeonggi-do (KR)

(73) Assignee: TELOFARM, INC., Seoul (KR)

( * ) Notice: Subject to any disclaimer, the term of this patent is extended or adjusted under 35 U.S.C. 154(b) by 195 days.

(21) Appl. No.: 17/045,800

(22) PCT Filed: Apr. 10, 2019

(86) PCT No.: PCT/KR2019/004249
§ 371 (c)(1),
(2) Date: Oct. 7, 2020

(87) PCT Pub. No.: WO2019/199041
PCT Pub. Date: Oct. 17, 2019

(65) Prior Publication Data
US 2021/0063377 A1    Mar. 4, 2021

(30) Foreign Application Priority Data
Apr. 12, 2018 (KR) .......................... 10-2018-0042830

(51) Int. Cl.
*G01N 27/22*      (2006.01)
*G01N 33/24*      (2006.01)

(52) U.S. Cl.
CPC ........... *G01N 33/246* (2013.01); *G01N 27/22* (2013.01)

(58) Field of Classification Search
CPC .... G01N 27/22; G01N 27/223; G01N 33/246; G01R 31/50
See application file for complete search history.

(56) References Cited

U.S. PATENT DOCUMENTS

| | | | | |
|---|---|---|---|---|
| 3,864,974 A | * | 2/1975 | Rauchwerger | ........ G01F 23/263 73/304 C |
| 4,122,718 A | * | 10/1978 | Gustafson | ............. G01F 23/263 73/304 C |

(Continued)

FOREIGN PATENT DOCUMENTS

| | | | | |
|---|---|---|---|---|
| AU | B-75275/94 | * | 5/1998 | ............. G01R 27/26 |
| CN | 10516016 B | * | 8/2015 | ............. G01N 27/00 |

(Continued)

OTHER PUBLICATIONS

Futagawa et. al. "Fabrication of a low leakage current type impedance sensor with shielding structure to detect a low water content of soil for slope failure prognostics", Sensors and Actuators A 271(2018)383-388. (Year: 2018).*

(Continued)

*Primary Examiner* — Giovanni Astacio-Oquendo
*Assistant Examiner* — Dilara Sultana
(74) *Attorney, Agent, or Firm* — Harness, Dickey & Pierce, PLC

(57) ABSTRACT

A device for measuring a moisture content in soil according to an aspect of the present invention comprises: a conductive wire structure which can be inserted into soil, includes a first and a second conductive wire, and is formed to have a predetermined structure, the first and the second conductive wire being insulatively coated and extending in parallel to and adjacent to each other; a capacitance measurement circuit for measuring the capacitance between the first and the second conductive wire by using an alternating current power source; and a moisture content calculation unit for calculating a moisture content of the soil by using the measured capacitance.

4 Claims, 5 Drawing Sheets

(56) References Cited

U.S. PATENT DOCUMENTS

| | | | | |
|---|---|---|---|---|
| 4,389,900 | A | * 6/1983 | Gutierrez | ................ G01W 1/14 |
| | | | | 73/304 C |
| 5,097,703 | A | * 3/1992 | Peter | ..................... G01F 23/265 |
| | | | | 73/304 C |
| 2013/0134994 | A1 | 5/2013 | Futagawa et al. | |

FOREIGN PATENT DOCUMENTS

| | | |
|---|---|---|
| JP | 2005-227199 A | 8/2005 |
| JP | 2011-145231 A | 7/2011 |
| KR | 20-0354371 Y1 | 6/2004 |
| KR | 10-2010-0095096 A | 8/2010 |

OTHER PUBLICATIONS

Office Action from corresponding Korean Patent Application No. 10-2018-0042830, dated Oct. 15, 2019.
International Search Report from corresponding PCT Application No. PCT/KR2019/004249, dated Jul. 16, 2019.

* cited by examiner

DEVICE FOR MEASURING MOISTURE CONTENT IN SOIL

CROSS-REFERENCE TO RELATED APPLICATIONS

This application is a National Phase entry of PCT Application No. PCT/KR2019/004249, filed on 10 Apr. 2019, which claims benefit of and priority to Korean Patent Application 10-2018-0042830, filed on 12 Apr. 2018. The entire disclosure of the applications identified in this paragraph are incorporated herein by reference.

FIELD

The present invention relates to a device for measuring a moisture content in soil.

BACKGROUND

It is very important to manage a moisture content in soil while plants are grown. When a moisture content around roots is high, roots absorb water well so as to perform transpiration well. However, when a moisture content is excessive, respiration of roots becomes difficult due to the lack of air around roots and it is difficult to increase microorganisms in soil around roots so that the lack of nutrients supplied to plants is caused. Accordingly, it is necessary to measure a moisture content in soil and to adjust the moisture content to maintain an adequate moisture content. Also, even when plants are watered, it is necessary to check a precise moisture content in soil so as to supply enough water necessary in a growth and development state of plants.

Due to the above reason, a method of measuring a moisture content in soil has been used in the field of growing plants and there are a tensiometer method and a time domain reflectometry (TDR) method as representative examples.

The tensiometer method uses a force of soil to attract water. When a porous plaster cup is filled with water and buried, the water moves into the soil through the porous cup. Here, when the water and a water content in the soil are in equilibrium, the water content is obtained by measuring a negative pressure of pores of the soil using a suction gauge or a mercury liquid manometer.

In the TDR method, probes configured to emit and receive a high-frequency signal are laid at a distance and a water content is measured using a dielectric constant of soil which is extracted from a time in which the emitted high-frequency signal is reflected and returns.

The tensiometer method has disadvantages such as a complicated sensor structure, a high price, and a small measurement range. Also, the TDR method measures a water content between end points of two probes according to a measurement principle and has a disadvantage of being limited to local area measurement. To overcome this, sensors may be installed at several points. However, a problem that a measurement region of each sensor is also limited to a local part still remains. Also, when a plurality of sensors are installed, it is impossible to avoid an increase in a total cost.

SUMMARY

Technical Problem

The present invention is directed to providing a moisture content measurement device for measuring a moisture content in soil, which has a simple structure, is priced low, and is capable of measuring a moisture content in soil over a larger area than a desired area.

Technical Solution

One aspect of the present invention provides a moisture content measurement device for measuring a moisture content in soil. The moisture content measurement device includes a conductive wire structure which is insertable into soil, includes insulatively-coated first and second conductive wires parallel to each other and extending adjacently, and has a certain structure, a capacitance measurement circuit configured to measure capacitance between the first and second conductive wires using alternating current (AC) power, and a moisture content calculation unit configured to calculate the moisture content in soil using the measured capacitance.

The moisture content calculation unit may calculate the moisture content in soil using a relationship in which the moisture content in soil is in proportion to the measured capacitance.

The conductive wire structure may further include a ground conductive wire parallel and extending adjacently to the first and second conductive wires and connected to a ground. Here, the moisture content calculation unit may calculate the moisture content in soil using a relationship in which the measured capacitance is reduced according to an increase of the moisture content in soil.

The moisture content calculation unit may calculate the moisture content in soil on the basis of first and second capacitance values previously measured using the capacitance measurement circuit corresponding to known first and second moisture contents.

The conductive wire structure may have a zigzag shape or a coil structure.

Another aspect of the present invention provides a moisture content measurement device for measuring a moisture content in soil. The moisture content measurement device includes a conductive wire structure which is insertable into soil, includes insulatively-coated first and second conductive wires parallel to each other and extending adjacently and a ground conductive wire parallel and extending adjacently to the first and second conductive wires and connected to a ground, and has a certain structure, a leakage current measurement circuit configured to apply AC power to the first and second conductive wires and to measure a leakage current leaking through the ground conductive wire, and a moisture content calculation unit configured to calculate the moisture content in soil using the measured leakage current.

The moisture content calculation unit may calculate the moisture content in soil using a relationship in which the moisture content in soil is in proportion to the measured leakage current.

The moisture content calculation unit may calculate the moisture content in soil on the basis of first and second leakage current values previously measured using the leakage current measurement circuit corresponding to known first and second moisture contents.

The conductive wire structure may have a zigzag shape or a coil structure.

Advantageous Effects

According to the present invention, there are effects such as a simple structure, a low cost, and a larger area than a desired area, in which moisture content in soil is measured.

DETAILED DESCRIPTION

Figure 1:
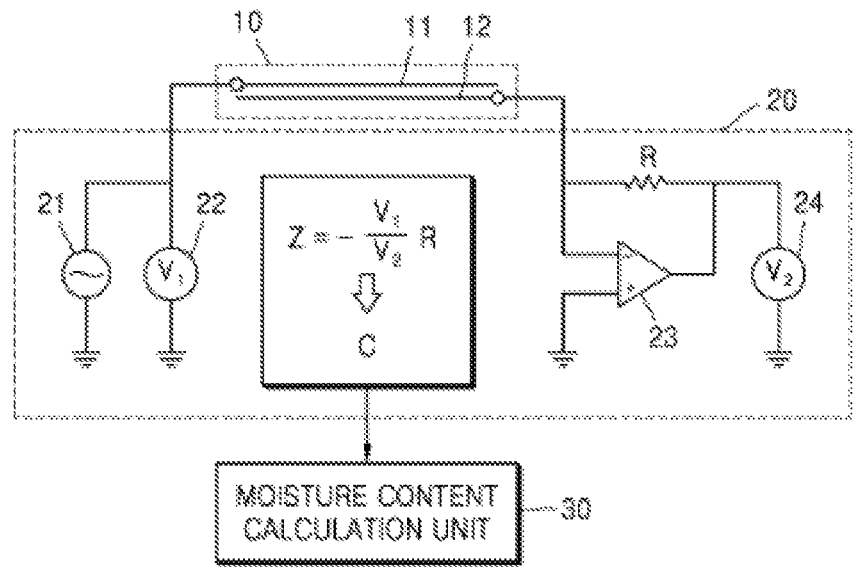
FIG. 1 illustrates components of a device for measuring a moisture content in soil according to a first embodiment of the present invention.

Hereinafter, exemplary embodiments of the present invention will be described in detail with reference to the drawings. Hereinafter, throughout the description and the attached drawings, substantially like elements will be referred to as like reference numerals and a repetitive description thereof will be omitted. Also, in a description of the embodiments of the present invention, a detailed description of well-known functions or components of the related art will be omitted when it is deemed to obscure understanding of the embodiments of the present invention.

FIG. 1 illustrates components of a device for measuring a moisture content in soil according to a first embodiment of the present invention.

The device according to the embodiment may include a conductive wire structure 10, a capacitance measurement circuit 20, and a moisture content calculation unit 30.

The conductive wire structure 10 is configured to be inserted into soil to measure a moisture content therein and includes insulatively-coated first and second conductive wires 11 and 12 disposed to be parallel to each other and to adjacently extend.

Since a dielectric is present between the first and second conductive wires 11 and 12 due to the insulative coating, the conductive wire structure 10 may be a sort of capacitor with the first and second conductive wires 11 and 12 as both electrodes thereof. Capacitance of the conductive wire structure 10, that is, capacitance between the first and second conductive wires 11 and 12 has a certain value according to a structure (size, shape, or the like) of the conductive wire structure 10.

When the conductive wire structure 10 comes into contact with moisture, the moisture is present between and near the first and second conductive wires 11 and 12 so that dielectric permittivity of the dielectric between the first and second conductive wires 11 and 12 varies. Here, as moisture in contact increases, the dielectric permittivity further increases. Since capacitance is in proportion to dielectric permittivity, as moisture in contact increases, the capacitance of the conductive wire structure 10 increases.

Figure 2:
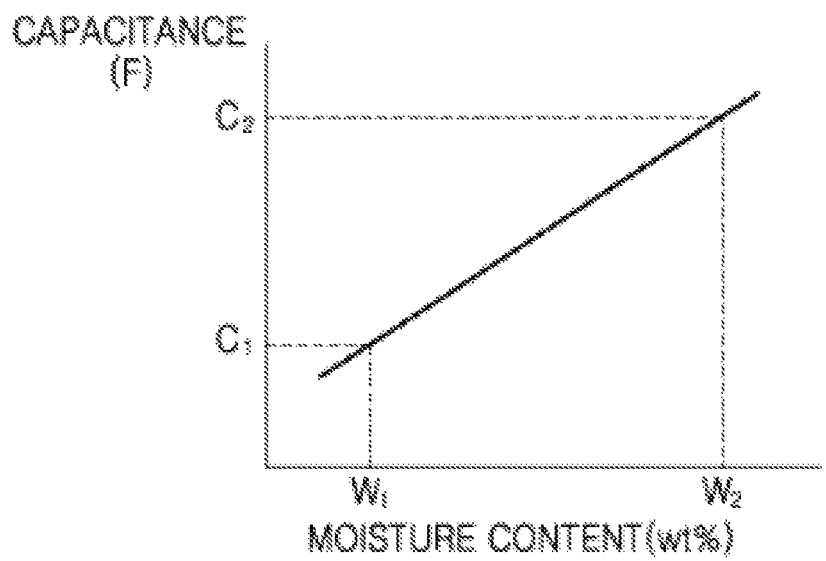
FIG. 2 is a graph illustrating a relationship between a moisture content and capacitance in the device according to the first embodiment of the present invention.

In the embodiment of the present invention, using this principle, a moisture content in soil is measured by inserting the conductive wire structure 10 into the soil and measuring the capacitance of the conductive wire structure 10. That is, according to the moisture content in soil, an amount of moisture, which comes into contact with the conductive wire structure 10 inserted into the soil, varies according to the moisture content in soil. Here, as the moisture content increases, the capacitance of the conductive wire structure 10 increases. Using this relationship, the moisture content in soil may be measured by measuring the capacitance of the conductive wire structure 10. The applicant can see that a moisture content and capacitance are in proportion to each other as a result of performing a test of measuring the capacitance of the conductive wire structure 10 while varying a moisture content in a soil sample. FIG. 2 is a graph illustrating a relationship between a moisture content in soil and capacitance.

The structure of the conductive wire structure 10 may be formed freely according to an area (extent, depth, and the like) to measure a moisture content in soil thereof. As one of simplest example, the conductive wire structure 10 may be formed to have a linear structure, may be formed to have a zigzag shape over the area to be measured, or may be formed to have a coil shape. As a length of the conductive wire structure 10 increases, a contact area with moisture increases so that accuracy and reliability may further increase.

Figure 3:
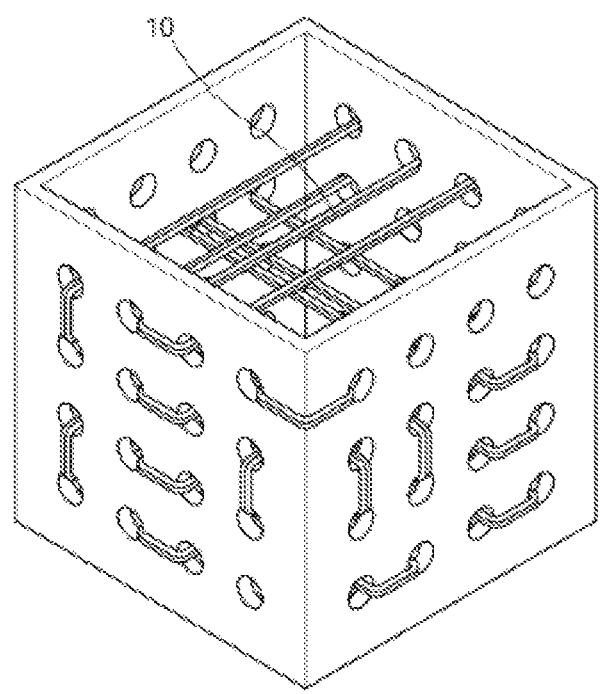
FIG. 3 illustrates an example of a structure of a conductive wire structure 10.
Figure 4:
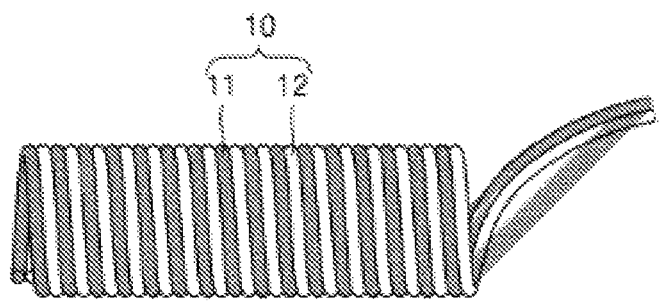
FIG. 4 illustrates another example of the structure of the conductive wire structure 10.

As an example of the structure of the conductive wire structure 10, FIG. 3 illustrates a structure in which the conductive wire structure 10 extends lengthwise in a zigzag shape over a certain extent and a certain depth to be measured. As another example of the structure of the conductive wire structure 10, FIG. 4 illustrates a cylindrical coil structure.

Referring back to FIG. 1, the capacitance measurement circuit 20 measures capacitance of the conductive wire structure 10, that is, capacitance between the first and second conductive wires 11 and 12 using an alternating current (AC) power source.

In the embodiment, although a circuit using an automatic balancing bridge is exemplified as an example of the capacitance measurement circuit 20, capacitance measurement may be performed using a variety of other measurement methods, for example, a bridge method, a resonance method, a voltage/current (I-V) method, and the like.

The capacitance measurement circuit 20 may include an AC power source 21, a first voltmeter 22, a resistor R, an operational amplifier 23, and a second voltmeter 24. The AC power source 21 is connected between one end of the first conductive wire 11 and a ground to supply an AC voltage, and the other end of the first conductive wire 11 is opened. The first voltmeter 22 is connected between the one end of the first conductive wire 11 and the ground and measures a voltage $V_1$ of the first conductive wire 11. One end of the second conductive wire 12 is opened, and one end of the resistor R is connected to the other end of the second conductive wire 12. An inverting terminal of the operational amplifier 23 is connected to the one end of the resistor R, a non-inverting terminal thereof is connected to the ground, and an output terminal is connected to the other end of the resistor R. The second voltmeter 24 is connected between the output terminal of the operational amplifier 23 and the ground and measures a voltage $V_2$ of the output terminal of the operational amplifier 23.

Impedance Z between the first and second conductive wires 11 and 12 may be measured using the voltage $V_1$ of the first voltmeter 22, the voltage $V_2$ of the second voltmeter 24, and the resistor R according to the following equation.

$$Z = -\frac{V_1}{V_2}R \qquad \text{[Equation 1]}$$

When the impedance Z is known, it is possible to know the capacitance between the first and second conductive wires 11 and 12.

The moisture content calculation unit 30 calculates a moisture content in soil, into which the conductive wire structure 10 is inserted, using capacitance measured using the capacitance measurement circuit 20. The moisture content calculation unit 30 may calculate the moisture content in soil using the above-described principle in which a moisture content in soil is in proportion to capacitance.

To allow the moisture content in soil to be calculated using a proportional relationship between the moisture content and the capacitance, first and second capacitance values previously measured using the capacitance measurement circuit 20 may be stored, corresponding to first and second known moisture contents, in the moisture content calculation unit 30. Referring to FIG. 2, when a first moisture content $W_1$, a capacitance value $C_1$ corresponding thereto, a second moisture content $W_2$, and a capacitance value $C_2$ corresponding thereto are known, a moisture content corresponding to a random measured capacitance value may be calculated using a proportional relationship.

When the conductive wire structure 10 is exposed in the air, a moisture content may be zero %. When the conductive wire structure 10 is submerged in the water, a moisture content may be 100%. Accordingly, when respective capacitance values measured in an air-exposed state and a water-submerged state of the conductive wire structure 10 having a certain structure are stored and capacitance is measured while the conductive wire structure 10, which maintains the structure, is inserted into soil, a moisture content in soil may be calculated using a measured capacitance value on the basis of the capacitance value corresponding to the moisture content of zero % and the capacitance value corresponding to the moisture content 100%.

Figure 5:
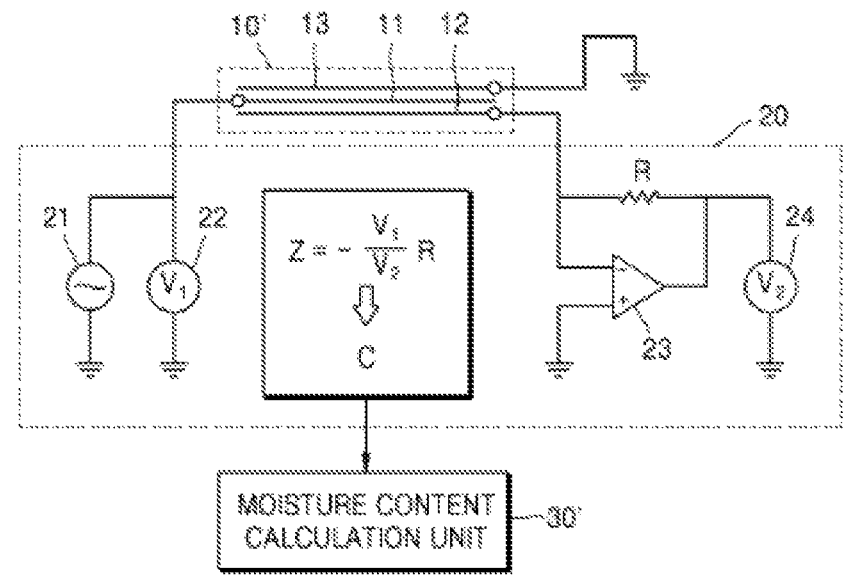
FIG. 5 illustrates components of a device for measuring a moisture content in soil according to a second embodiment of the present invention.

FIG. 5 illustrates components of a device for measuring a moisture content in soil according to a second embodiment of the present invention.

The device according to the embodiment may include a conductive wire structure 10', the capacitance measurement circuit 20, and a moisture content calculation unit 30'.

In the device shown in FIG. 1, when a conductive path is formed in soil to be measured due to a certain cause so that the soil is connected to a ground, a current leakage phenomenon occurs through moisture in the soil. Here, an amount of a leakage current is in proportion to a moisture content in soil and capacitance measured by the capacitance measurement circuit 20 is not real capacitance of the conductive wire structure 10 and is shown as a false measured value caused by the leakage current. The capacitance measured by the capacitance measurement circuit 20 is not a real capacitance value of capacitance between the first and second conductive wires 11 and 12. However, as the moisture content increases, the leakage current increases so that the capacitance is measured as a reduced value.

In the embodiment, to cause the phenomenon, a conductive path is artificially formed in soil near the first and second conductive wires 11 and 12 and is connected to the ground. Here, the conductive wire structure 10' is formed by adding a ground conductive wire 13, which extends adjacently and is parallel to the first and second conductive wires 11 and 12 and is connected to the ground, to the conductive wire structure 10 of FIG. 1. Then, moisture, which come into contact with the first and second conductive wires 11 and 12, also comes into contact with the ground conductive wire 13 so that a leakage current flows through the ground conductive wire 13. The ground conductive wire 13 may not be coated or may be coated with enamel or the like which has a relatively low resistance against AC so as to be conducted with soil and moisture in soil. Accordingly, when AC power is applied to the first and second conductive wires 11 and 12, a leakage current occurs through the ground conductive wire 13. As a moisture content increases, the leakage current increases and a measured capacitance value is reduced.

Figure 6:
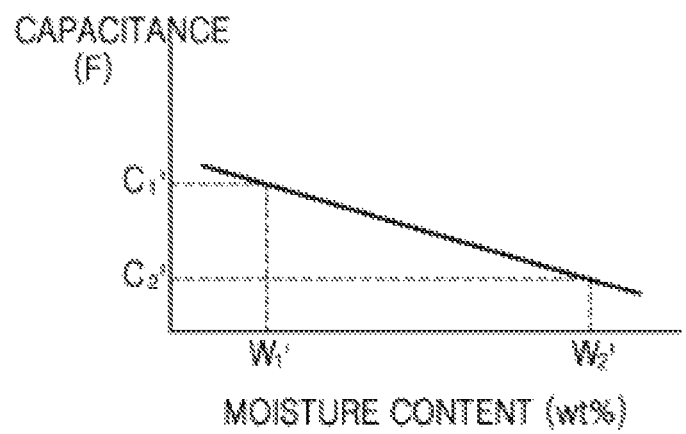
FIG. 6 is a graph illustrating a relationship between a moisture content and a measured capacitance value in the device according to the first embodiment of the present invention.

As a result of an experiment of measuring capacitance of the conductive wire structure 10' using the capacitance measurement circuit 20 while varying a moisture content in a soil sample, the applicant may check that a measured capacitance value is linearly reduced as the moisture content increases. FIG. 6 is a graph illustrating a relationship between a moisture content in soil and a measured capacitance value.

The moisture content calculation unit 30' calculates a moisture content in soil, into which the conductive wire structure 10' is inserted, using capacitance measured using the capacitance measurement circuit 20. On the contrary to the moisture content calculation unit 30, the moisture content calculation unit 30' may calculate a moisture content in soil using a relationship in which the measured capacitance value is linearly reduced as the moisture content in soil increases.

To allow the moisture content in soil to be calculated using the relationship between the moisture content and the measured capacitance value, first and second capacitance values previously measured using the capacitance measurement circuit 20 may be stored, corresponding to first and second known moisture contents, in the moisture content calculation unit 30'. Referring to FIG. 6, when a first moisture content $W_1'$, a capacitance value $C_1'$ corresponding thereto, a second moisture content $W_2'$, and a capacitance value $C_2'$ corresponding thereto are known, a moisture content corresponding to a random measured capacitance value may be calculated using the relationship between the moisture content and the measured capacitance value.

When the conductive wire structure 10' is exposed in the air, a moisture content may be zero %. When the conductive wire structure 10' is submerged in the water, a moisture content may be 100%. Accordingly, when respective capacitance values measured in an air-exposed state and a water-submerged state of the conductive wire structure 10' having a certain structure are stored and capacitance is measured while the conductive wire structure 10', which maintains the structure, is inserted into soil, a moisture content in soil may be calculated using a measured capacitance value on the basis of the measured capacitance value corresponding to the moisture content of zero % and the measured capacitance value corresponding to the moisture content 100%.

Figure 7:
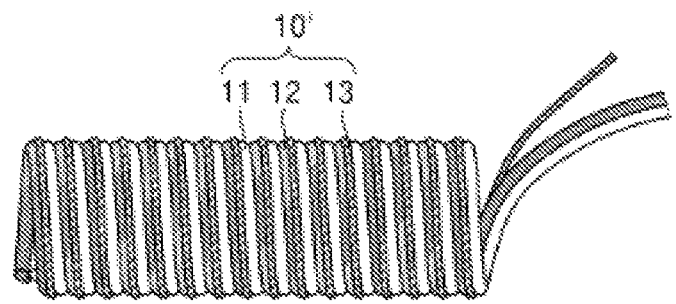
FIG. 7 illustrates an example of a structure of a conductive wire structure 10'.

Like the conductive wire structure 10 of FIG. 1, the conductive wire structure 10' of FIG. 5 may also be formed to have a variety of structures such as a linear shape, a zigzag shape, a coil shape, and the like. FIG. 7 illustrates an example in which the conductive wire structure 10' has a cylindrical coil structure.

Figure 8:
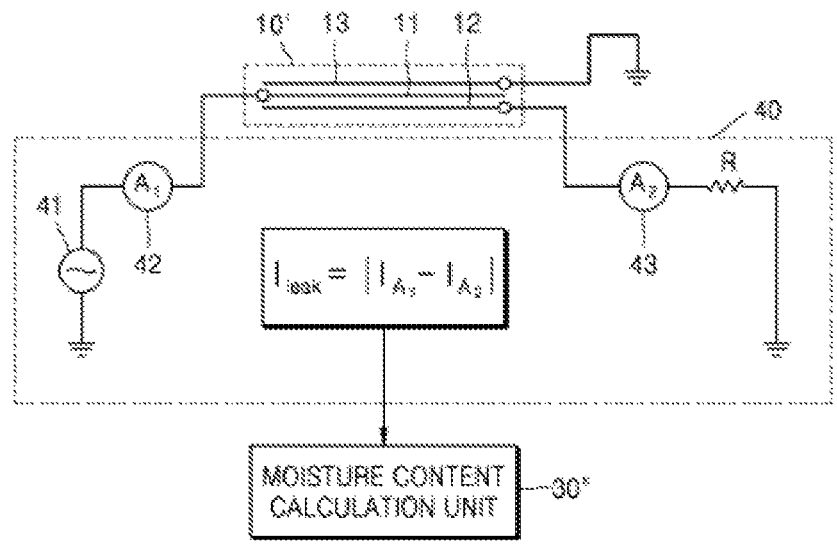
FIG. 8 illustrates components of a device for measuring a moisture content in soil according to a third embodiment of the present invention.

FIG. 8 illustrates components of a device for measuring a moisture content in soil according to a third embodiment of the present invention.

The device according to the embodiment may include the conductive wire structure 10', a leakage current measurement circuit 40, and a moisture content calculation unit 30".

As described above with respect to the second embodiment, when AC power is applied to the first and second conductive wires 11 and 12, a leakage current occurs through the ground conductive wire 13 and the leakage current increases in proportion to an increase of a moisture content. In the embodiment, this is used so that a moisture content in soil is measured by measuring a leakage current flowing through the ground conductive wire 13.

The leakage current measurement circuit 40 applies AC power to the first and second wires 11 and 12 of the conductive wire structure 10' and measures a leakage current leaking through the ground conductive wire 13.

The leakage current measurement circuit 40 may include an AC power source 41, a first ammeter 42, a second ammeter 43, and a resistor R. The AC power source 41 is connected between one end of the first ammeter 42 and the ground and supplies an AC voltage. The first ammeter 42 has the other end connected to one end of the first conductive wire 11 and measures a current $I_{A1}$ supplied to the first conductive wire 11. The second ammeter 43 has one end connected to the other end of the second conductive wire 12 and the resistor R is connected between the other end of the second ammeter 43 and the ground so that the second ammeter 43 measures a current $I_{A2}$ output through the second conductive wire 43.

A level of a leakage current $I_{leak}$, which flows through the ground conductive wire 13, may be measured using a difference between the current $I_{A1}$ of the first ammeter 42 and the current $I_{A2}$ of the second ammeter 43 according to the following equation.

$$I_{leak} = |I_{A1} - I_{A2}|$$ [Equation 2]

Figure 9:
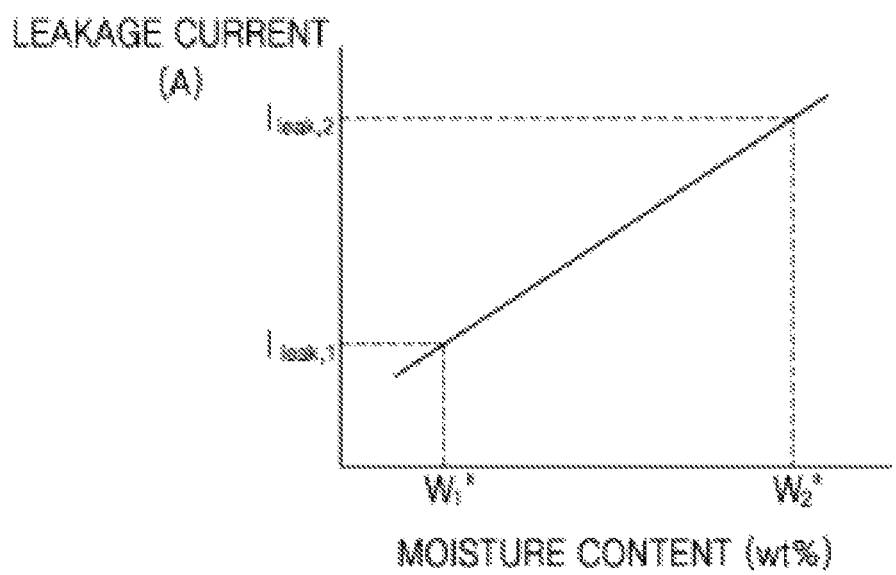
FIG. 9 is a graph illustrating a relationship between a moisture content and a current leak in the device according to the third embodiment of the present invention.

FIG. 9 is a graph illustrating a relationship between a moisture content in soil and a leakage current flowing through the ground conductive wire 13. As shown in the drawing, a moisture content and a leakage current are in proportion to each other.

The moisture content calculation unit 30" calculates a moisture content in soil, into which the conductive wire structure 10' is inserted, using a leakage current measured using the leakage current measurement circuit 40. The moisture content calculation unit 30" may calculate the moisture content in soil using a principle in which a moisture content in soil is in proportion to a leakage current.

To allow the moisture content in soil to be calculated using a proportional relationship between the moisture content and the leakage current, first and second leakage current values previously measured using the leakage current measurement circuit 40 may be stored, corresponding to first and second known moisture contents, in the moisture content calculation unit 30". Referring to FIG. 9, when a first moisture content $W_1$", a leakage current value $I_{leak,1}$ corresponding thereto, a second moisture content $W_2$", and a leakage current value $I_{leak,2}$ corresponding thereto are known, a moisture content corresponding to a random measured leakage current value may be calculated using the proportional relationship.

When the conductive wire structure 10' is exposed in the air, a moisture content may be zero %. When the conductive wire structure 10' is submerged in the water, a moisture content may be 100%. Accordingly, when respective leakage current values measured in an air-exposed state and a water-submerged state of the conductive wire structure 10' having a certain structure are stored and a leakage current is measured while the conductive wire structure 10', which maintains the structure, is inserted into soil, a moisture content in soil may be calculated using a measured leakage current value on the basis of the measured leakage current value corresponding to the moisture content of zero % and the measured leakage current value corresponding to the moisture content 100%.

According to the embodiments of the present invention, since the conductive wire structure 10 or 10' to be inserted into soil includes two or three conductive wires, the conductive wire structure 10 or 10' may be formed with a desired size and shape so as to measure a moisture content in soil in a variety of areas as necessary as well as a small area.

When the conductive wire structure 10 or 10' is formed to have a coil structure as shown in FIG. 4 or 7, a surface area which comes into contact with soil is increased in a small area. Also, a length or diameter of a coil is decreased to perform measurement in a local area and is increased to perform measurement in a wide area. The size of the coil may vary according to a size of an area to be measured. Also, a distribution of moisture content may be checked by inserting the conductive wire structures 10 or 10' in several parts of soil, and a distribution of moisture content according to a depth may be checked by inserting the conductive wire structures 10 or 10' at several depths.

When the conductive wire structure 10 or 10' is formed to have a coil structure, a particular porous medium is inserted into a coil, and then a sealed structure in which only a central inlet is exposed and other parts are blocked from the outside is formed and buried in soil, moisture in soil flows into the porous medium in the coil due to a capillary phenomenon so as to be in equilibrium with whole moisture of soil. Accordingly, a sensor capable of measuring a moisture content in soil regardless of a type of a medium to be measured (rock wool, cocopeat, ferrite, soil, or the like) may be formed.

The embodiments of the present invention may be shown as functional block components and a variety of processing operations. The functional blocks may be implemented through a variety of numbers of hardware and/or software components which implement particular functions. For example, an embodiment may employ integrated circuit components such as a memory, processor, logic, look-up table, and the like which are capable of performing a variety functions under the control of one or more microprocessors or other control devices. Like the components of the present invention being executable using software programs or software elements, the embodiment may include a data structure, processes, routines, or a variety of algorithms which are implemented through a combination of other programming components and may be implemented as programming and scripting languages such as C, C++, Java, an assembler, and the like. Functional aspects may be implemented as an algorithm executed by one or more processors. Also, the embodiment may employ conventional arts for electronic environment settings, signal processing, data processing, and/or the like. The terms such as "mechanism," "element," "means," and "component" may be widely used and are not limited to mechanical and physical components. The terms may include the meaning of a series of routines of software in connection with a processor and the like.

Particular executions described in the embodiment are merely examples, and the scope of the embodiment is not limited to any methods. For a concise specification, a description of conventional electronic components, control systems, software, and other functional aspects of the systems will be omitted. Also, connection of lines or connection members between components shown in the drawings are exemplarily shown as functional connection and/or physical or circuit connections and may be a variety of replaceable or additional functional connections, physical connection, or circuit connections in a real apparatus. Also, unless stated in detail such as "essential," "significant," and the like, a component may not be essential for applying of the present invention.

The exemplary embodiments of the present invention have been described above. It should be understood by one of ordinary skill in the art that the present invention may be implemented as a modified form without departing from the essential features of the present invention. Therefore, the disclosed embodiments should be considered not in a limitative view but a descriptive view. The scope of the present invention will be shown in the claims not in the above description, and all differences within an equivalent range thereof should be construed as being included in the present invention.

What is claimed is:

1. A moisture content measurement device for measuring a moisture content in soil, the moisture content measurement device comprising:
   a conductive wire structure which is insertable into soil, wherein the conductive wire structure comprises insulatively-coated first and second conductive wires parallel to each other and extending adjacently, and a ground wire parallel and extending adjacently to the first and second conductive wires and connected to a ground, and has a certain structure;
   a leakage current measurement circuit configured to apply AC power to the first and second conductive wires and to measure a leakage current leaking through the ground wire; and
   a moisture content calculation unit configured to calculate the moisture content in soil using the measured leakage current,
   wherein the leakage current measurement circuit comprises an AC power source, a first ammeter including a first end and a second end, a second ammeter including a first end and a second end, and a resistor, wherein the AC power source is connected between the first end of the first ammeter and the ground and is configured to supply an AC voltage, wherein the second end of the first ammeter is connected to the first conductive wire, wherein the first ammeter is configured to measure a first current supplied to the first conductive wire, wherein the first end of the second ammeter is connected to the second conductive wire, wherein the resistor is connected between the second end of the second ammeter and the ground, wherein the second ammeter is configured to measure a second current output through the second conductive wire, wherein the leakage current, which flows through the ground wire, is measured by the difference between the first current of the first ammeter and the second current of the second ammeter.

2. The moisture content measurement device of claim 1, wherein the moisture content calculation unit is configured to calculate the moisture content in soil using a relationship in which the moisture content in soil is in proportion to the measured leakage current.

3. The moisture content measurement device according to claim 2, wherein the moisture content calculation unit is configured to calculate the moisture content in soil on the basis of first and second leakage current values previously measured using the leakage current measurement circuit corresponding to known first and second moisture contents.

4. The moisture content measurement device of claim 1, wherein the conductive wire structure has a zigzag shape or a coil structure.

* * * * *